United States Patent [19]

Basta

[11] 4,146,035
[45] Mar. 27, 1979

[54] ENDOCARDIAL ELECTRODE AND APPLICATOR THEREFOR

[76] Inventor: Edward Basta, 300 N. State St., Suite 4930, Chicago, Ill. 60610

[21] Appl. No.: 836,011

[22] Filed: Sep. 23, 1977

[51] Int. Cl.² ............................................. A61N 1/04
[52] U.S. Cl. .................. 128/404; 128/419 P
[58] Field of Search .......... 128/404, 418, 419 P, 128/407–409, 2.06 E, 2.1 E, DIG. 4

[56] References Cited

U.S. PATENT DOCUMENTS

| Re. 27,569 | 2/1973 | Ackerman | 128/418 |
| 3,087,486 | 4/1963 | Kilpatrick | 128/418 X |
| 3,416,534 | 12/1968 | Quinn | 128/418 |
| 3,516,412 | 6/1970 | Ackerman | 128/418 |
| 3,533,403 | 10/1970 | Woodson | 128/404 X |
| 3,680,544 | 8/1972 | Shinnick et al. | 128/418 X |
| 3,754,555 | 8/1973 | Schmitt | 128/418 |
| 3,814,104 | 6/1974 | Irnick et al. | 128/418 |
| 3,844,292 | 10/1974 | Bolduc | 128/418 |
| 3,880,169 | 4/1975 | Stare et al. | 128/418 |
| 3,952,742 | 4/1976 | Taylor et al. | 128/418 X |
| 3,974,834 | 8/1976 | Kane | 128/418 |
| 4,000,745 | 1/1977 | Goldberg | 128/418 |

FOREIGN PATENT DOCUMENTS 284244  1/1971  U.S.S.R. .................................. 128/418

Primary Examiner—Lee S. Cohen
Attorney, Agent, or Firm—Wegner, Stellman, McCord, Wiles & Wood

[57] ABSTRACT

A cone-shaped electrode for endocardial use as two insulated conductors which extend transthoracicly to a point exterior of the patient when the electrode is implanted. The connector is coupled to the conductors to provide an assembly which is connected with a pacemaker providing electrical impulses for ventricular stimulation. The pacemaker may be attached to the connector during implantation or immediately thereafter. A cannula-type applicator for the assembly is disclosed.

8 Claims, 9 Drawing Figures

U.S. Patent  Mar. 27, 1979  Sheet 1 of 2  4,146,035
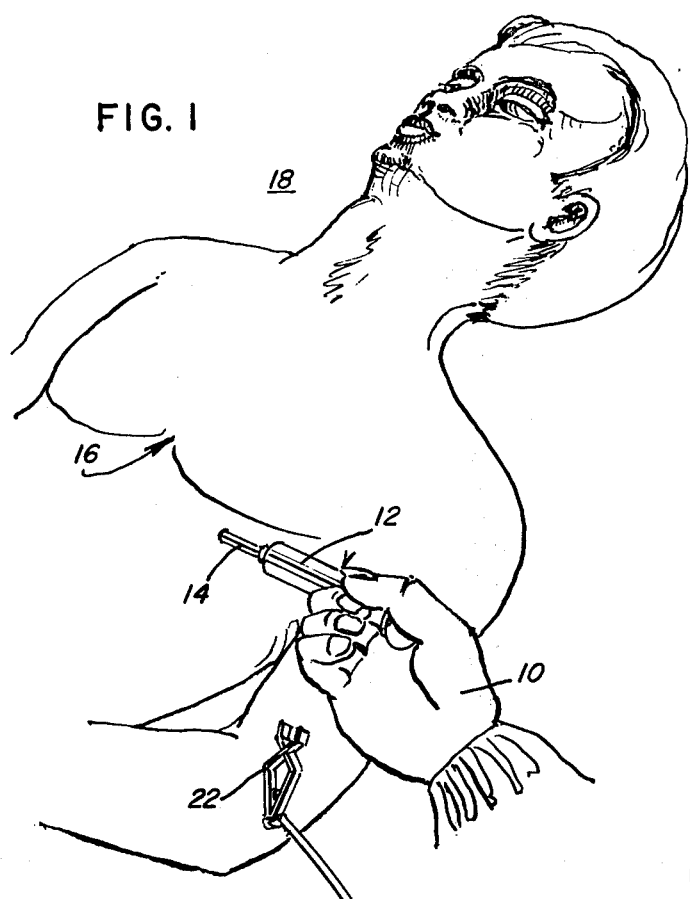
FIG. 1
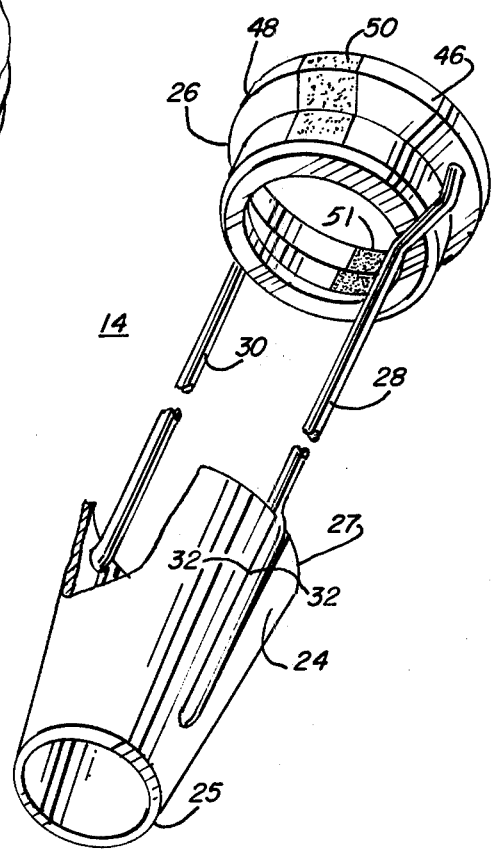
FIG. 2
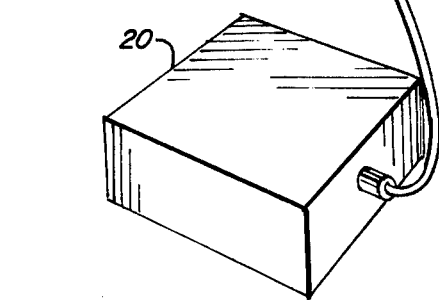
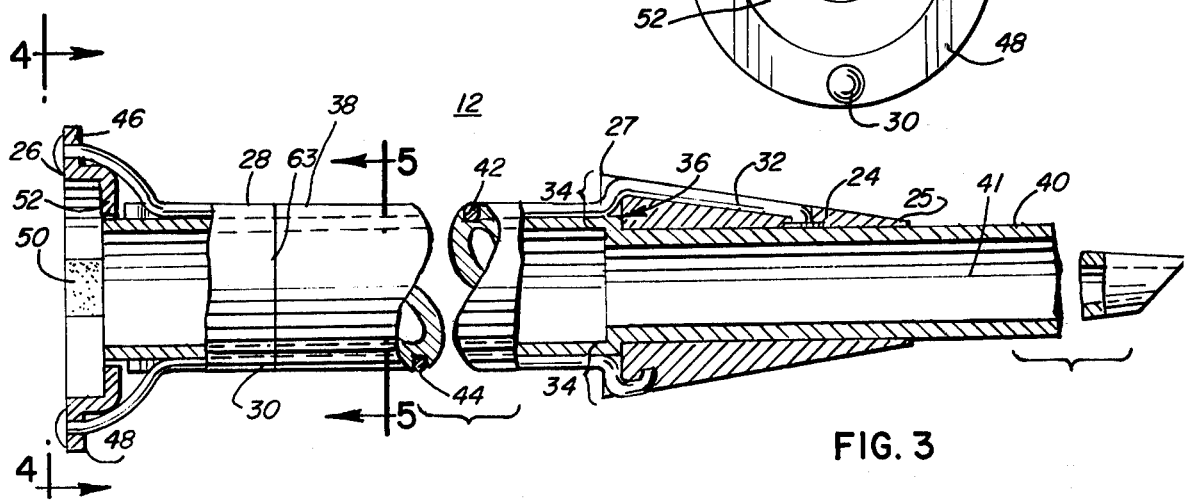
FIG. 4
FIG. 3

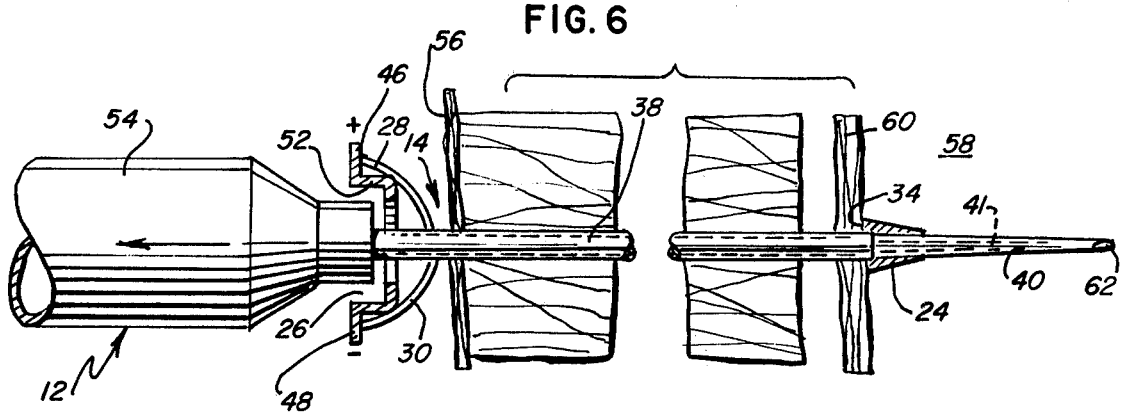
FIG. 6
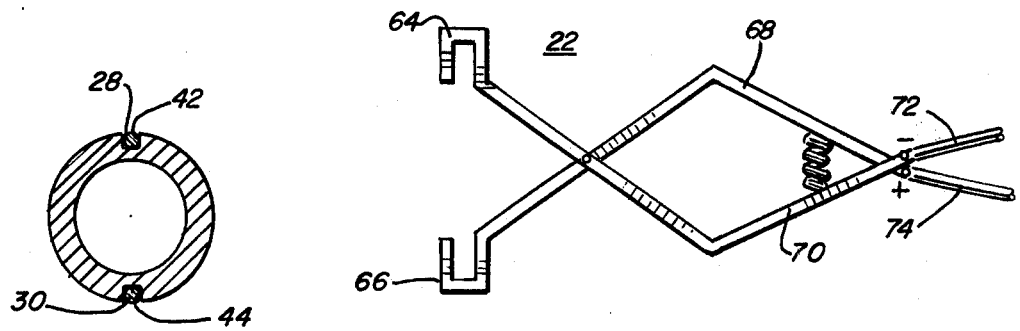
FIG. 5
FIG. 9
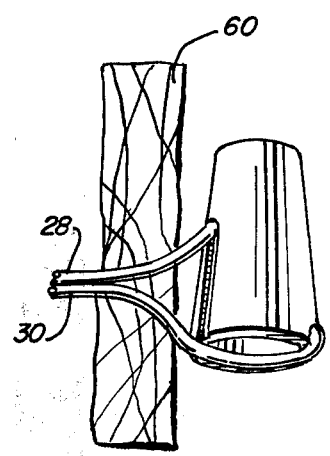
FIG. 7
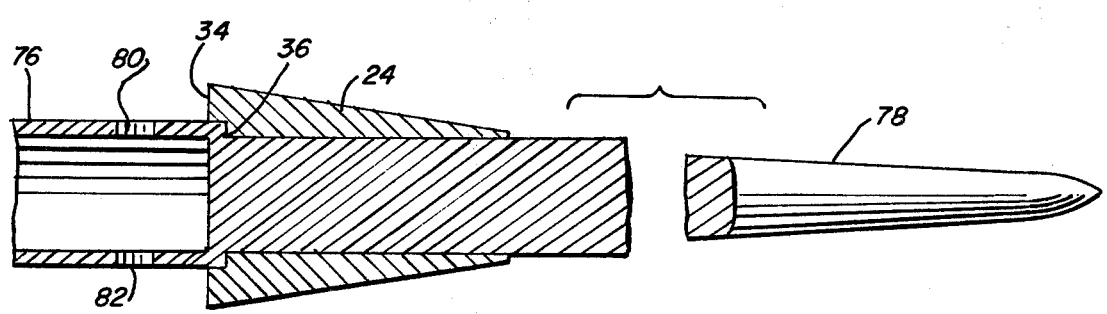
FIG. 8

ENDOCARDIAL ELECTRODE AND APPLICATOR THEREFOR

BACKGROUND OF THE INVENTION

This invention relates to medical instruments and devices and, more particularly, to endocardial electrodes for transthoracic insertion and a cannula-type applicator therefor.

Stimulation of the heart by electrical impulses have aided in the treatment of many heart dysfunctions. The so-called pacer or pacemaker instruments include an external signal source which provides electrical impulses to a connector which is coupled to conductors extending through the thorax to an endocardial electrode. These instruments permit reliable pacing so long as the electrode is in contact with the selected ventricular cavity.

A number of endocardial electrode assemblies have been proposed, but many transthoracicly-inserted electrode assemblies are not provided with a suitable external connector. This results in an undesirable delay in connecting the newly implanted electrode to the pacemaker.

SUMMARY OF THE INVENTION

In accordance with the present invention, an electrode assembly for endocardial use includes a cone-shaped electrode having a passageway along its axis which receives a cannula-type applicator. Two insulated conductors attached to the electrode extend through the thorax from the heart and are coupled to an external connector which is adapted to be quickly coupled to an electronic pacemaker. The cannula-type applicator implants the electrode and is withdrawn and removed after implantation. The electronic pacemaker may be connected to the assembly during or immediately after implantation.

It is a feature of the present invention to provide an endocardial electrode assembly having an electrode which may be easily and reliably inserted into the heart.

It is another feature of the invention to provide an electrode assembly having a connector adapted to quickly connect with an electronic pacer or pacemaker.

Yet another feature of the invention is to provide a cannula-type applicator for inserting the endocardial electrode assembly into the heart through the thorax.

Other features and advantages will become apparent when considering the following specification in combination with the drawing in which:

BRIEF DESCRIPTION OF THE DRAWINGS

FIG. 1 is a perspective view of a patient about to undergo a transthoracic implantation of the electrode assembly;

FIG. 2 is a perspective view of an electrode assembly of the present invention;

FIG. 3 is a cross-sectional view of the electrode assembly of FIG. 2 mounted on a cannula-type applicator;

FIG. 4 is an end view of the connector taken along the lines 4—4 of FIG. 3;

FIG. 5 is a cross-sectional view of the applicator taken along the lines 5—5 of FIG. 3;

FIG. 6 is a diagrammatic view of an electrode assembly and the applicator extending through the thorax and into the heart;

FIG. 7 is another diagrammatic view of the endocardial electrode within the heart after the applicator has been withdrawn and removed;

FIG. 8 is another cannula-type applicator; and,

FIG. 9 is a schematic view of a pacemaker connected to a clip which may be quickly secured to the electrode assembly after it has been implanted.

DESCRIPTION OF THE PREFERRED EMBODIMENT

Referring to FIG. 1, the physician's hand 10 grasps an applicator 12 for transthoracic insertion of an endocardial electrode assembly 14 in the thorax 16 of a patient 18. Applicator 12 is of the cannula type and is usually inserted laterally through the fourth inner space about 1½ to 2 inches to the left of the peristernal line, substantially perpendicular to the chest wall, slightly inclined toward the medial plane. The tip of the applicator reaches the ventricular cavity after approximately 3½ to 4 inches of penetration. Reaching of the ventricular cavity is detected by aspirating the applicator in a manner to be described below.

Although the electrode assembly is discussed in the context of the ventricular cavity, it is suitable for use in any portion of the heart having the requisite cooperating tissue so long as the electrode is in contact with the myocardium.

Upon insertion of the assembly 14, the physician withdraws applicator 12, leaving the endocardial electrode assembly implanted within patient 18. The assembly 14 is then coupled to pacemaker 20 through clip 22. The assembly 14 has a metallic electrode which applies a stimulus to the heart in response to an electrical impulse from pacemaker 20.

Referring to FIGS. 2-5, the endocardial electrode assembly is shown having a metallic electrode 24, usually of platinum construction, a connector 26 with conductors 28 and 30 connecting the connector 26 with the metallic electrode 24. The length of the conductors 28 and 30 is sufficient to extend from the heart to a point exterior of the patient. The metallic electrode 24 is generally of an annular shape with the outer surface tapering along the axis of the electrode to form a cone having a forward edge 25 and a rear edge 27. As best seen in FIG. 2, the electrode is provided with outwardly opening channel 32 which extends axially along the outer surface of the electrode for substantially the entire length thereof. The outwardly opening channel 32 receives conductor 28 which is attached to the forward portion of electrode 24. Conductor 30 is attached to the rear portion of electrode 24. This arrangement assures that the electrode will be properly placed against the inner wall of the ventricular chamber, as will be explained below. Conductors 28 and 30 are suitably attached to electrode 24 by well-known techniques, such as soldering, or the like.

Electrode 24 has a rear surface 34 which extends radially inward from rear edge 27. The rear surface 34 is of sufficient width to abut ledge 36 of the cannula 38 of applicator 12. Lance 40 is integrally formed with cannula 38 and extends forwardly from ledge 36. The lance may be provided with a passage 41. Electrode 24 is mounted over the proximal end of lance 40. Rear surface 34 and ledge 36 cooperate to restrict rearward axial movement of the electrode during insertion of the assembly. The combination of the electrode 24 and the lance 40 provides a smooth even taper forward from edge 27. For example, if cannula 38 has an outer diameter equivalent to a 14-gauge wire, the diameter of electrode 24 at ridge 27 would be equivalent to a 12-gauge wire, the diameter of forward edge 25 would be equivalent to a 14-gauge wire, and the lance 40 would taper evenly to the angled penetration point.

Cannula 38 is provided with symmetrically opposed outwardly opening channels 42 and 44 along its surface which extend from ledge 36 rearwardly toward the proximal end thereof. The channels 42 and 44 receive conductors 28 and 30, respectively, during insertion of the electrode assembly.

Connector 26 is in the form of an annular ring formed by conductive plates 46 and 48 secured together by electrically insulative spacers 50 and 51, as best seen in FIG. 4. The connector may be of any suitable type which is capable of being quickly connected to a clip from the pacemaker 20. The connector shown in FIG. 4 is particularly suitable since conductive plates 46 and 48 are opposite each other, and a recessed inner section 52 is provided to generally conform to the shape of the proximal end of cannula 38.

Referring to FIG. 6, syringe 54 of known construction is secured to cannula 38, thus forming applicator 12. As shown, endocardial electrode assembly 14 is mounted on applicator 12 and extends transthoracicly between epidermis 56 and ventricular cavity 58. Lance 40 is shown to have pierced the ventricular wall 60. The resiliency of the wall 60 is sufficient to cause it to return toward its original position after being traversed by lance 40 and electrode 24. The appropriate penetration of lance 40 is determined by aspirating the syringe 54, causing blood to flow into inlet 62 of the angled point through passage 41 which is in communication with the barrel of the syringe. The applicator 14 is then removed by the physician and, since rear surface 34 abuts the ventricular wall 60, electrode 24 is captured within the ventricular cavity 58.

The physician then manipulates connector 26 so that its diameter is generally perpendicular to conductors 28 and 30. This manipulation is accomplished by pulling on conductor 28, which is longer than conductor 30 (see FIG. 2), to roll or cant electrode 24 onto its side adjacent the ventricular wall 60, as shown in FIG. 7. This technique assures that a larger surface area of electrode 24 is adjacent wall 60. The physician then manually connects a pacer-connected clip to connector 26 if he has not previously done so.

The applicator electrode complex of FIG. 6 is actually a special disposable intercardiac needle which could also be provided with a prefilled disposable syringe 54, the prefilling being of a dose-amount of adrenaline or comparable heart stimulant. The complex will serve a dual purpose, first, as soon as the needle penetrates into the ventricular cavity, adrenaline or the like, is administered intracardiacally, which is done in practically all cardiac arrests to stimulate the cardiac fiber to contract and, second, the needle is pushed into a point where the mark 63 on the needle, see FIG. 3, will indicate that the electrode is in the ventricular cavity whereupon the needle is withdrawn, the lead 28 is manipulated to cant the electrode and the connector 26 is connected to the heart pacer for pacemaker stimulation.

A suitable pacer-connected clip is shown in FIG. 9. The clip 22 includes similar conductive cups 64 and 66 which are connected to arms 68 and 70 and engage conductive plates 46 and 48 on the connector 26. Electrical impulses from pacer 20 are provided through connecting leads 72 and 74 which may be coupled directly with conductive cups 64 and 66 or to arms 68 and 70.

In FIG. 3, a mark 63 is shown on the cannula 38 to indicate the location of the electrode in the heart.

Referring to FIG. 8, an alternate cannula and lance are shown. Specifically, cannula 76 is integrally connected with lance 78, and electrode 24 is retained thereon in a manner similar to that shown in FIG. 6. Lance 78 differs from the lance 40 shown in FIG. 6 in that lance 78 does not have a passageway with an inlet at its distal end. Rather, inlets 80 and 82 are provided in cannula 76 rearwardly of ledge 36. This particular structure assures the physician that the electrode 24 has reached the ventricular cavity 58. Specifically, by aspirating the syringe, blood will flow only after the lance and the electrode have pierced the ventricular wall 60.

The endocardial electrode of FIG. 8 may be implanted in a ventricular cavity in the following manner. The electrode and the cannula applicator will come in one unit already pre-assembled. The physician uses the needle to penetrate the thorax so that the lance and electrode extend into the ventricular cavity. The syringe is then aspirated to assure that the electrode is within the ventricular cavity. The applicator is then withdrawn. The longer lead 28 is manipulated to cant the electrode into a position approximating the showing of FIG. 7.

The physician manipulates the connector 26 so that its diameter is generally perpendicular to the conductors 28, 30 leading to the electrode, as discussed above. If not previously done, the leads from the pacemaker are attached to the connector 26 by means of the clip 22 gripping the plates 46, 48 of the connector.

I claim:

1. An endocardial electrode assembly for transthoracic insertion into the heart comprising:
    an annular metallic electrode generally of cone shape having a forward edge and a spaced-apart rear edge of larger diameter than said forward edge to define an outer surface therebetween, and a rear surface extending radially inward from said rear edge;
    an electrical connector adapted to be connected to an electric pacemaker providing electrical impulses; and
    electrical conductor means including a first and a second conductor, each connected between said connector and said electrode, said conductor means being of sufficient length to extend through the thorax, and said first conductor being longer than said second conductor.

2. The assembly of claim 1 further including a channel opening outwardly from the outer surface and extending between said forward edge and said rear edge, said channel adapted to receive said first conductor.

3. An endocardial electrode assembly for transthoracic insertion into the heart comprising:
    an annular metallic electrode generally of cone shape for applying a stimulus to the heart in response to an electrical impulse provided thereto;
    an electrical connector in the form of an annular ring having a first and a second conductive plate coupled together by electrically insulative material for connection with an electric pacemaker providing electrical impulses; and
    electrical conductor means connecting each conductive plate of said connector with said annular metallic electrode, said conductor means being of sufficient length to extend through the thorax.

4. The combination of an endocardial electrode assembly for transthoracic insertion into the heart and an applicator therefor comprising:

an annular metallic electrode generally of cone shape for applying a stimulus to the heart in response to an electrical impulse provided thereto, said electrode adapted to be mounted on a lance and having a forward edge and a spaced-apart rear edge of larger diameter than said forward edge to define an outer surface therebetween and a rear surface extending radially inward from said rear edge;

means for connecting said electrode to an electric pacemaker for providing said electrical impulse;

a syringe;

a cannula having a proximal and a distal end coupled to the syringe at said distal end;

a lance integrally formed with said cannula at said proximal end; and a radially extending ledge between the lance and the proximal end of said cannula, said ledge engaging said rear edge of said metallic electrode mounted on said lance.

5. The combination of claim 4 wherein said lance has a passageway communicating with the cannula and has an inlet at its end.

6. The combination of claim 4 wherein inlets are provided on said cannula adjacent said ledge.

7. A method of implanting an endocardial electrode within a ventricular cavity of the heart of a patient comprising:

disposing an electrode assembly on a cannula-type applicator having a syringe, a cannula, a lance, and inlet means in communication with the syringe through the cannula, said electrode assembly having an annular cone-shaped electrode connected by conductor means to a connector adapted to be connected to an electric pacemaker;

inserting the applicator with said electrode assembly so that the lance with said electrode thereon extend through the thorax and into the ventricular cavity;

aspirating the syringe to determine if the cone-shaped electrode is within the selected atrial cavity;

withdrawing the applicator from the thorax leaving said electrode in the ventricular cavity; and causing the electrode of the electrode assembly to be adjacent the wall of the ventricular cavity and said connector external of said patient.

8. The method of claim 7 wherein said conductor means comprise first and second conductors secured between said electrode and said connector, said conductors being of unequal length, said connector being ring-shaped, further including the step of:

aligning the connector in a manner substantially perpendicular to the conductors thereby assuring that the electrode is adjacent the wall of the ventricular cavity.

* * * * *